(12) United States Patent
Pieper et al.

(10) Patent No.: US 10,258,710 B1
(45) Date of Patent: Apr. 16, 2019

(54) CONTAINER FOR HOLDING VOLATILE MATERIALS

(71) Applicant: S. C. JOHNSON & SON, INC., Racine, WI (US)

(72) Inventors: Gregory G. Pieper, Spring Grove, IL (US); Richard D. Maggard, Jr., Oak Creek, WI (US)

(73) Assignee: S. C. JOHNSON & SON, INC., Racine, WI (US)

( * ) Notice: Subject to any disclaimer, the term of this patent is extended or adjusted under 35 U.S.C. 154(b) by 20 days.

(21) Appl. No.: 15/713,206

(22) Filed: Sep. 22, 2017

(51) Int. Cl.
*A61L 9/12* (2006.01)
*B65D 1/02* (2006.01)
*B65D 41/04* (2006.01)

(52) U.S. Cl.
CPC ............ *A61L 9/127* (2013.01); *B65D 1/0246* (2013.01); *B65D 41/0421* (2013.01); *A61L 2209/133* (2013.01)

(58) Field of Classification Search
CPC ............... A61L 9/127; A61L 2209/133; A61L 9/00–9/22; B65D 1/0246; B65D 41/0421; B65D 1/00–1/48; B65D 41/00–41/62; B65D 1/023; B65D 1/0223; B05B 17/0684; B05B 17/0676
USPC ............................ 215/44, 43, 40; 239/34–60
See application file for complete search history.

(56) References Cited

U.S. PATENT DOCUMENTS

| | | | |
|---|---|---|---|
| 3,802,590 A | 4/1974 | Culver | |
| 3,822,811 A | 7/1974 | Landen | |
| 6,104,867 A | 8/2000 | Stathakis et al. | |
| 6,446,880 B1 * | 9/2002 | Schram | B05B 17/0646 222/570 |
| 6,768,865 B2 | 7/2004 | Stathakis et al. | |
| 6,779,672 B2 | 8/2004 | Kano et al. | |
| 6,792,199 B2 | 9/2004 | Levine et al. | |
| 7,014,055 B2 | 3/2006 | Kano et al. | |
| 7,017,829 B2 * | 3/2006 | Martens, III | B05B 17/0646 239/326 |
| 7,244,398 B2 * | 7/2007 | Kotary | A61L 9/042 239/34 |
| 7,303,143 B2 | 12/2007 | Davis et al. | |
| 7,352,960 B2 | 4/2008 | Hafer et al. | |
| 7,389,943 B2 * | 6/2008 | Jaworski | A01M 1/205 239/102.2 |

(Continued)

FOREIGN PATENT DOCUMENTS

| | | |
|---|---|---|
| FR | 2839296 A1 | 11/2003 |
| JP | 2000238822 A | 9/2000 |
| JP | 4276726 B2 | 6/2009 |

*Primary Examiner* — Jason J Boeckmann
*Assistant Examiner* — Juan C Barrera
(74) *Attorney, Agent, or Firm* — Quarles & Brady LLP

(57) ABSTRACT

A refill for dispensing a volatile material includes a bottle having a body defined by at least one sidewall and a neck extending outwardly from the at least one sidewall. The neck includes a rim at an upper end thereof, the neck being defined by an inner surface, a top surface, and an outer surface. The refill further includes a plug and a wick having a first end positioned within the bottle and a second end extending out of the bottle, the wick further defining a longitudinal axis. The plug is coupled to the neck of the bottle, the plug retaining the wick within the bottle. At least a portion of the inner surface of the rim is tapered at an angle of between about 2 and about 9 degrees with respect to the longitudinal axis.

21 Claims, 6 Drawing Sheets

(56) References Cited

U.S. PATENT DOCUMENTS

| | | |
|---|---|---|
| 7,416,766 B2 | 8/2008 | Trent et al. |
| 7,643,734 B2 | 1/2010 | Wefler |
| 7,743,952 B2 | 6/2010 | Auer et al. |
| 7,832,579 B2 | 11/2010 | Lohrman et al. |
| 7,886,899 B2 | 2/2011 | Frutin |
| 8,025,189 B2 | 9/2011 | Salameh |
| 8,235,232 B2 | 8/2012 | Isogai et al. |
| 8,485,398 B2 | 7/2013 | Kneer |
| 8,496,129 B2 | 7/2013 | Isogai et al. |
| 9,375,739 B2 | 6/2016 | Ivri |
| 9,694,967 B2 | 7/2017 | Salameh |
| 2004/0026464 A1 | 2/2004 | Granger et al. |
| 2005/0195598 A1 | 9/2005 | Dancs et al. |
| 2005/0211579 A1 | 9/2005 | Makita |
| 2005/0284952 A1* | 12/2005 | Davis ............... A01M 1/2077 239/44 |
| 2006/0175425 A1 | 8/2006 | McGee et al. |
| 2006/0289570 A1 | 12/2006 | Rohr |
| 2007/0080128 A1* | 4/2007 | Laveault ............... B65D 1/023 215/44 |
| 2010/0059601 A1 | 3/2010 | Bankers et al. |
| 2010/0215549 A1 | 8/2010 | Corda |
| 2012/0000880 A1 | 1/2012 | Im |
| 2013/0037580 A1 | 2/2013 | Armstrong et al. |
| 2013/0327327 A1 | 12/2013 | Edwards et al. |
| 2015/0367366 A1 | 12/2015 | Edwards et al. |
| 2016/0263602 A1 | 9/2016 | Ivri |
| 2016/0311589 A1 | 10/2016 | Wochele |
| 2017/0036824 A1 | 2/2017 | King |

\* cited by examiner

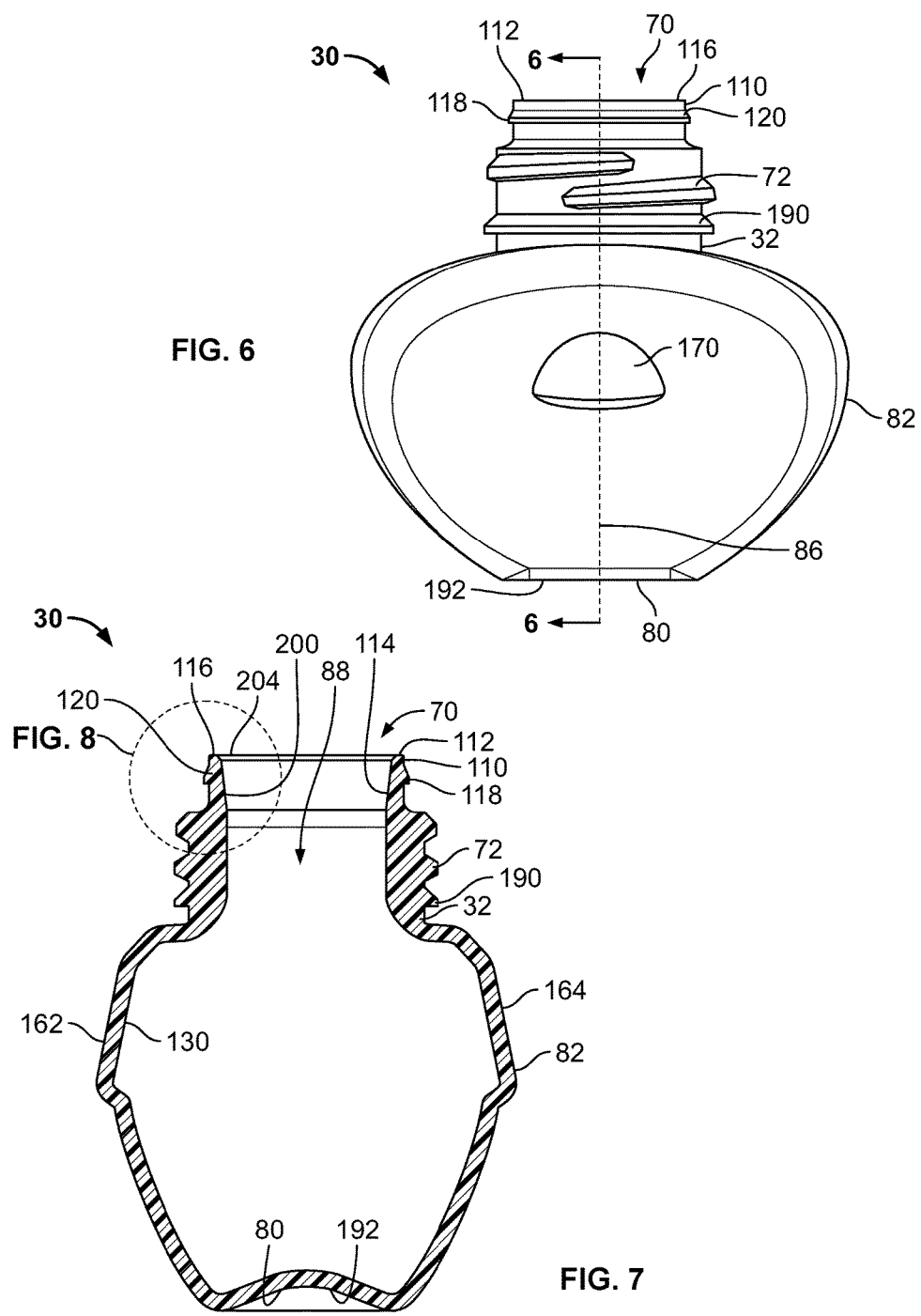

CONTAINER FOR HOLDING VOLATILE MATERIALS

BACKGROUND OF THE DISCLOSURE

1. Field of the Disclosure

The present disclosure generally relates to refills for use with dispensers, and, more specifically, to refills configured to reduce stresses in a neck of the refills.

2. Description of the Background of the Disclosure

Various volatile material dispensing devices are known in the prior art and generally comprise a dispenser and one or more refills having one or more volatile materials disposed therein. Typical volatile material dispensing mechanisms used in volatile material dispensing devices include a heating device and/or a fan to assist with the emanation of the volatile material from the refill(s).

Refills for dispensers generally include a bottle, a plug or wick holder that is inserted into a mouth within a neck of the bottle, and a wick that is retained by the plug, the wick having a first end in contact with the volatile material and a second end extending out of the bottle. The volatile material is moved from the bottle, through the first end of the wick to an end of the wick by capillary action. Surfaces defining the mouths of refills have varying geometry, depending on the type of material being used for the bottle itself. Further, the type of material used for such bottles can vary. Some bottles are made from glass, while some are made from plastic resins such as metallocene polypropylene (mPP) or Barex resins. In the fragrance oil delivery space, clear polymers have been found to develop stress cracking along a neck of the refill surrounding the mouth, especially when exposed to increasing temperature and bottle stress. While a portion of the stress cracking is believed to be due to selective absorption of stress cracking agents, i.e., from fragrance oils and/or solvents, a portion of the stress cracking is likely due to hoop or circumferential stress incurred by the bottle after the plug and wick have been inserted therein and after a cap is attached to the refill. It is believed that these stress cracking agents cause the formation of micro-yielded or stress-dilated zones, which reduce the yield strength of the polymer forming the bottle. A reduction in yield strength of the polymer can lead to crack initiation and fracture, which may worsen upon insertion of the plug and/or wick and/or attachment of the cap.

Much of the stress cracking of typical refill bottles comprising polymers forms in the neck of the bottle, e.g., adjacent the mouth of the bottle. Stress cracking is typically a result of stress on portions of the refill bottle. Because of the clamping of the neck by the wick holder, a number of stresses are created along an uppermost portion of the neck. In many instances, the stress cracking originates from a sealing surface and propagates to a medial portion of the neck. Since refill bottles must retain the fluid held therein, it is desirable to maintain a fluid seal between the plug and the bottle, and to also reduce the stress cracking that propagates adjacent the neck of the bottle. It would therefore be desirable to minimize the plug assembled tensile hoop stress that develops in the bottle neck finish while maintaining a normal seal pressure.

SUMMARY

According to one aspect, a refill for dispensing a volatile material includes a bottle comprising a body defined by at least one sidewall and a neck extending outwardly from the at least one sidewall. The neck includes a rim at an upper end thereof, wherein the rim is defined by an inner surface, a top surface, and an outer surface. The refill further includes a wick having a first end positioned within the bottle and a second end extending out of the bottle. The wick further defines a longitudinal axis. The refill further includes a plug coupled to the neck of the bottle, which retains the wick within the bottle. At least a portion of the inner surface of the rim is tapered at an angle of between about 2 and about 9 degrees with respect to the longitudinal axis.

According to another aspect, a refill for dispensing a volatile material includes a bottle having a body defined by at least one sidewall, and a neck extending outwardly from the at least one sidewall. The neck includes threading circumscribing at least a portion of the neck, and a rim at an upper end of the neck. The rim is defined by an inner surface, an outer surface, and a top surface extending between the inner and outer surfaces. The refill further includes a channel formed by the neck, such that a longitudinal axis is defined by the channel, and a wick having a first end positioned within the bottle and a second end extending out of the bottle, the wick being positioned within the channel. The refill further includes a plug coupled to the neck of the bottle, the plug retaining the wick within the bottle and comprising a well formed by walls of the plug. The refill further includes a cap attached to the bottle, the cap comprising a seal skirt that extends into the well when the cap is secured to the bottle. The inner surface of the rim is tapered at an angle of between about 3 and about 8 degrees with respect to the longitudinal axis.

BRIEF DESCRIPTION OF THE DRAWINGS

FIG. 6 is a front elevational view of the bottle of FIG. 5;

FIG. 7 is a cross-sectional view taken generally along the lines 6-6 of FIG. 6.

DETAILED DESCRIPTION OF THE DRAWINGS

The present disclosure is directed to refills for volatile material dispensers capable of vaporizing and dispensing the volatile materials. While the devices disclosed herein may be embodied in many different forms, several specific embodiments are discussed herein with the understanding that the embodiments described in the present disclosure are to be considered only exemplifications of the principles described herein, and the disclosure is not intended to be limited to the embodiments illustrated. Throughout the disclosure, the terms "about" and "approximately" mean plus or minus 5% of the number that each term precedes.

The use of the term "volatile material" herein refers to any volatile material that a consumer may desire to emit into an area surrounding one or more refills holding the volatile material(s) and/or a dispenser holding one or more refills.

Illustratively, the types of volatile materials may be, for example, a cleaner, an insecticide, an insect repellant, an insect attractant, a mold or mildew inhibitor, a fragrance, a disinfectant, an air purifier, an aromatherapy scent, an antiseptic, a positive fragrancing volatile material, an air-freshener, a deodorizer, or the like, and combinations thereof. Additives may be included in the volatile material, such as, for example, fragrances and/or preservatives.

Figure 1:
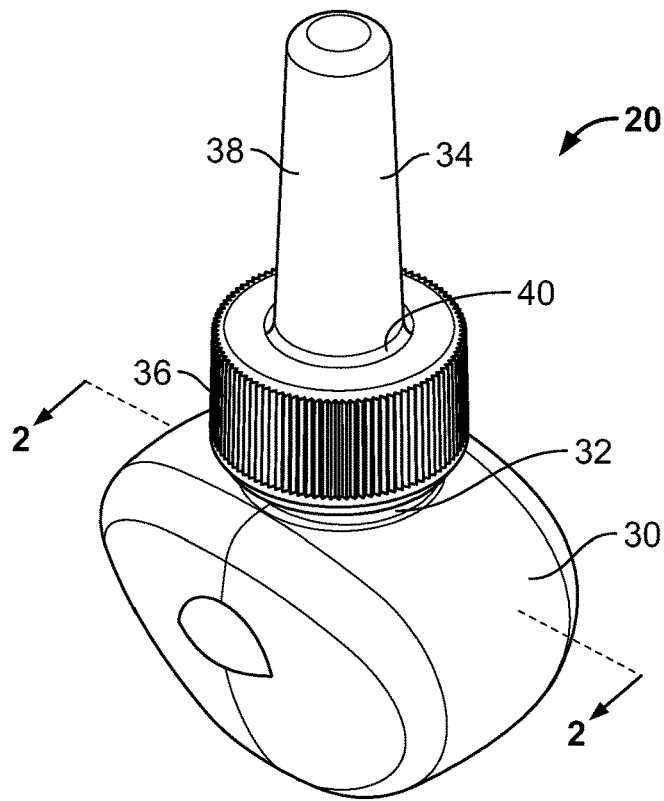
FIG. 1 is a front, top isometric view of a refill according to some aspects of the present disclosure.
Figure 2:
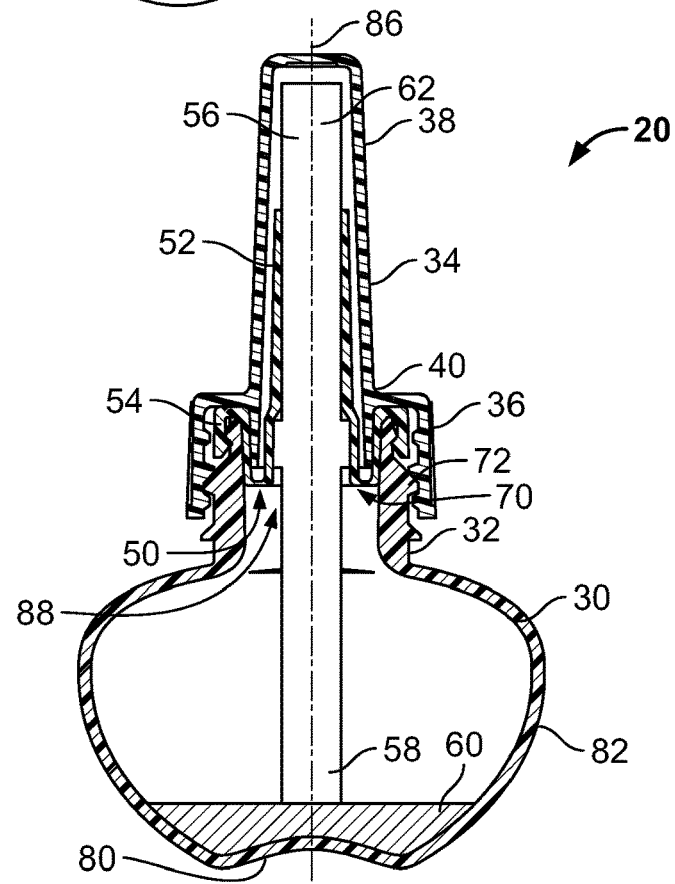
FIG. 2 is a cross-sectional view taken generally along the lines 2-2 of FIG. 1.
Figure 3:
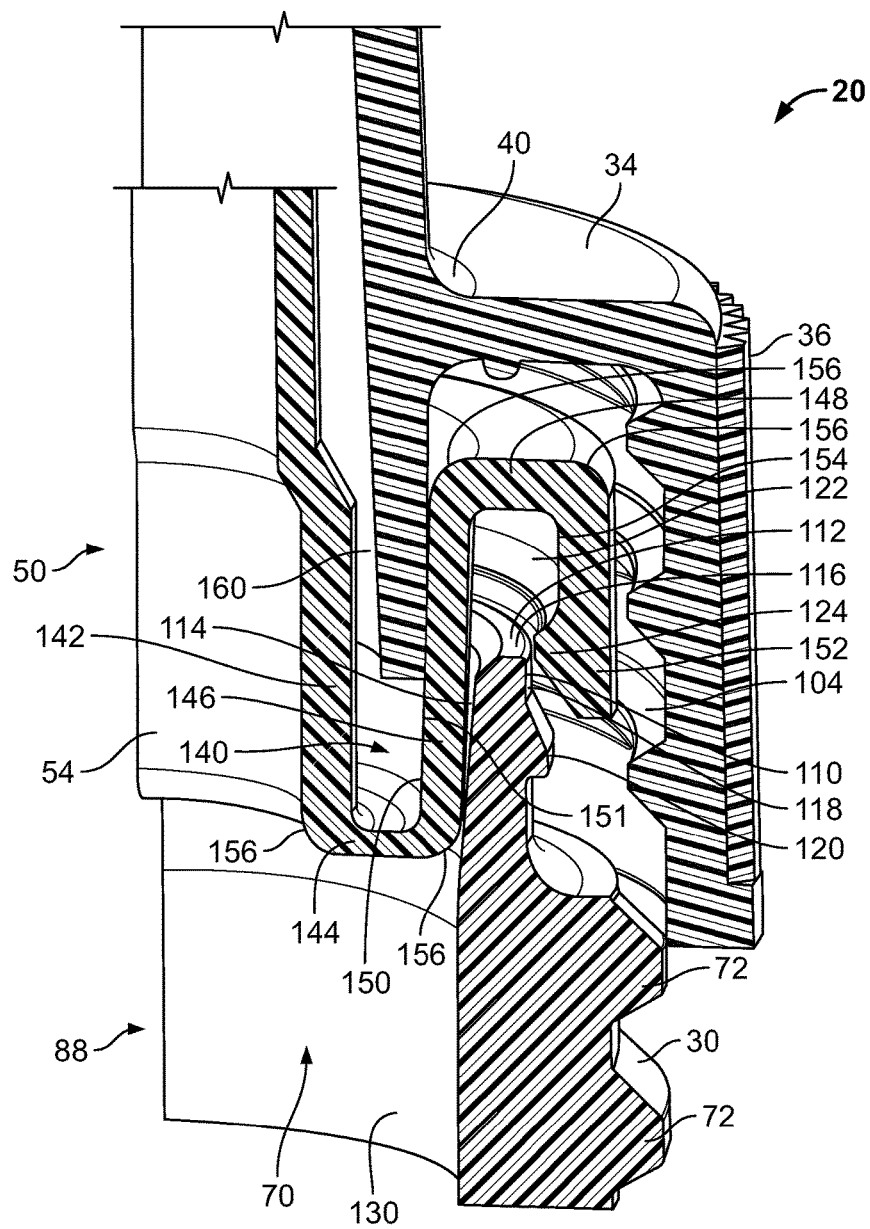
FIG. 3 is a partial cross-sectional view of the refill of FIG. 2 without a wick.

FIGS. 1-3 generally depict a refill 20 for use with a volatile material dispenser (not shown) that may be capable of actively or passively emanating a volatile material disposed within the refill 20 into the ambient environment. In some embodiments, the refill 20 is capable of insertion into and retention within the volatile material dispenser. Referring now to FIG. 1, the refill 20 generally includes a bottle 30 that holds a volatile material, wherein a cylindrical neck 32 extends upwardly from the bottle 30. The bottle 30 may be formed from glass, polymer, or another suitable material or materials. A cap 34 is shown secured to the neck 32 of the bottle 30. The cap 34 generally includes a securement portion 36 and a cover portion 38. The securement portion 36 may include threading along an inner surface thereof that may be used to secure the cap 34, for example, to the neck 32 of the bottle 30. The securement portion 36 and the cover portion 38 are connected at a joint 40.

Referring to FIG. 2, a front cross sectional view of the refill 20 is shown. As can be seen in FIG. 2, the refill 20 further includes a plug assembly 50 that is disposed within and attached to the neck 32 of the refill 20. The plug assembly 50 generally includes a sheath 52 and a base 54. The plug assembly 50 retains a wick 56 centrally within the bottle 30 and prevents leakage of volatile material 60 out of the bottle 30. A lower portion 58 of the wick 56 is in fluid communication with the volatile material 60 disposed within the bottle 30. The wick 56 extends upwardly through the neck 32 such that an upper portion 62 thereof is exposed to a surrounding environment when the cap 34 is removed.

The sheath 52 of the plug assembly 50 extends upwardly from a mouth 70 of the bottle 30 and surrounds a portion of the wick 56. The wick 56 may be any type of transportation mechanism such as, for example, typical wicks (of porous material), dip tubes, hollow tubes, and gravity fed surfaces or components, or any other suitable transportation mechanism.

Still referring to FIG. 2, the bottle 30 further includes a bottom wall 80 and at least one sidewall 82. The bottom wall 80 is depicted as being generally concave, however, the bottom wall 80 may be planar, or have any other suitable configuration. As illustrated in FIG. 2, the sidewall 82 extends upwardly from the bottom wall 80 and bows outwardly from a longitudinal axis 86 that extends through the wick 56. The sidewall 82 terminates at the neck 32 of the bottle 30. The wick 56 and the sheath 52 are inserted into a channel 88 defined by the neck 32 of the refill 20.

Figure 5:
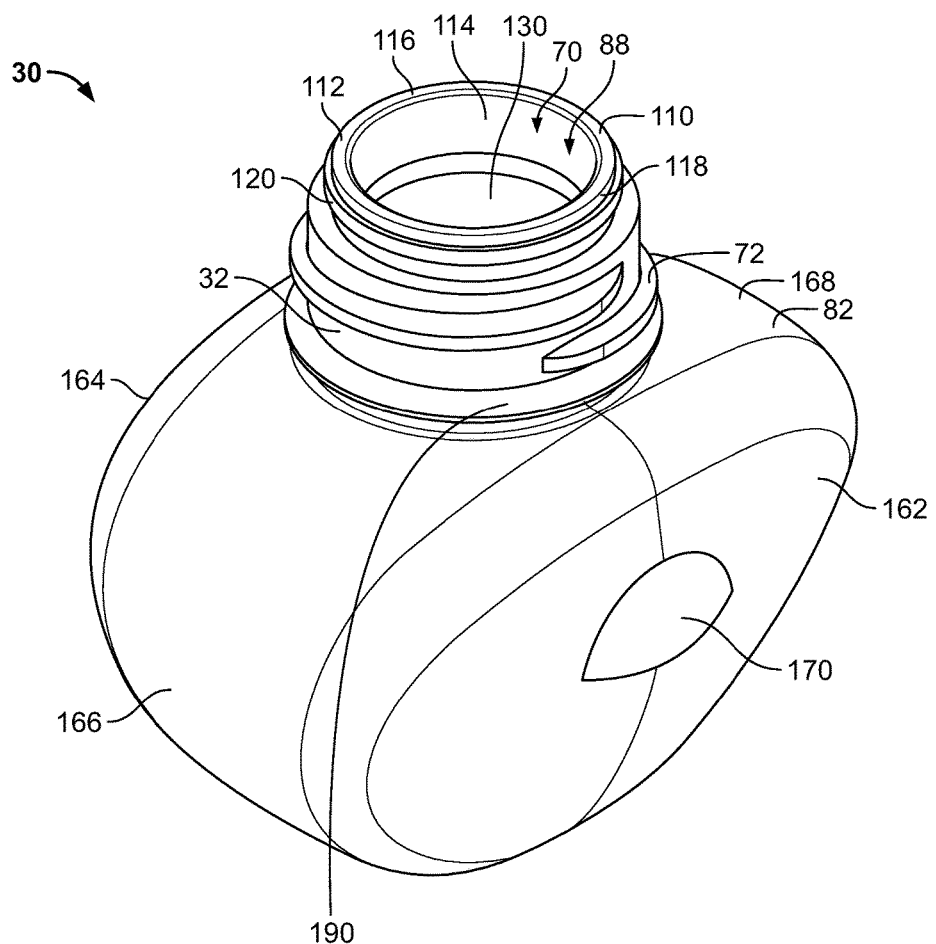
FIG. 5 is a front, top, and side isometric view of a bottle of the refill of FIG. 1.

Referring to FIG. 5, the sidewall 82 of the bottle 30 includes front and rear surfaces 162, 164 and first and second side surfaces 166, 168 connecting the front and rear surfaces 162, 164. The front surface 162 has a generally bulbous central portion and is generally curved inwardly at sides and a bottom thereof. The rear surface 164 may be a mirror image of the front surface 162, or may have a different configuration. In some embodiments, the rear surface 164 is generally planar. In some embodiments, a protrusion or design element 170 extends outwardly from the front surface 162, wherein the design element 170 may function to retain the refill 20 within a dispenser. While the bottle disclosed herein is shown as having a particular shape, the principles of the present invention may be applied to a refill having a bottle with any suitable shape.

Figure 4:
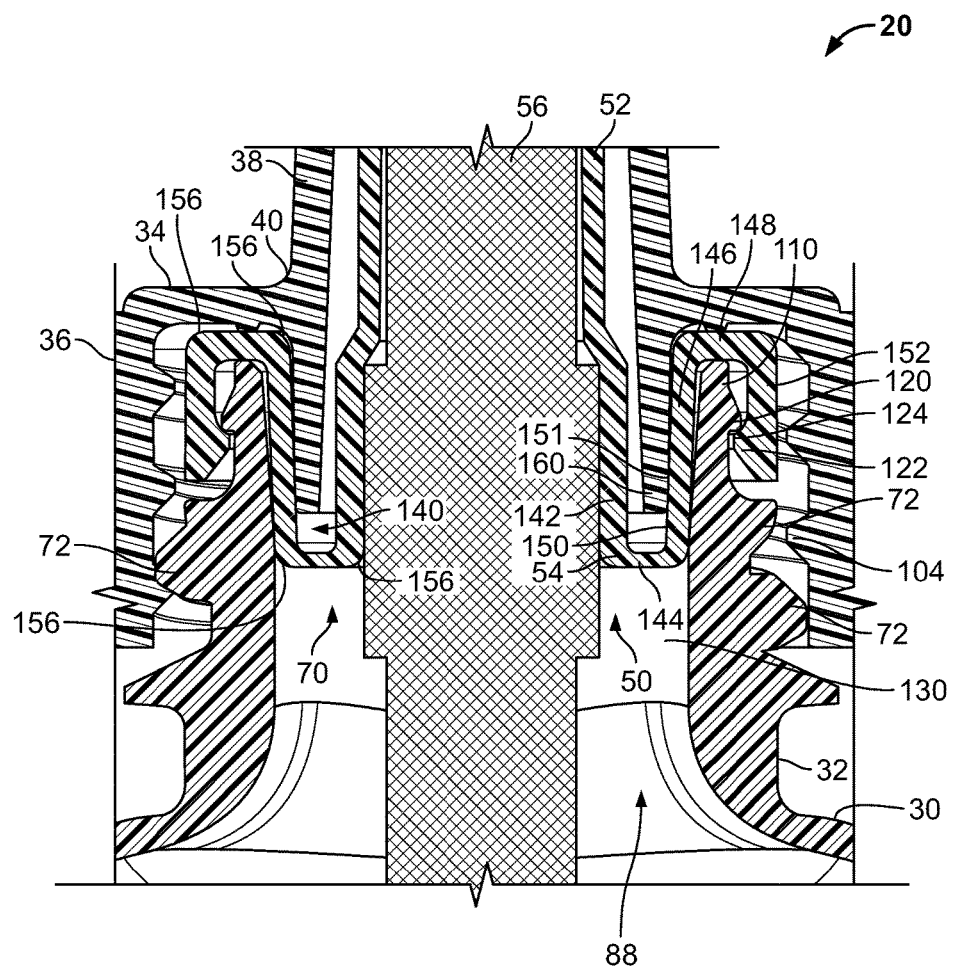
FIG. 4 is another partial cross-sectional view of the refill of FIG. 2.

Referring now to FIGS. 3 and 4, a first thread 72 is disposed on the neck 32 of the bottle 30 to aid in retaining the cap 34 thereon and/or to aid in retaining the refill 20 within the dispenser. The cap 34 includes a second thread 104 on an inner surface thereof that corresponds to, and is operable to receive the first thread 72. The first thread 72 and the second thread 104 comprise an exemplary securement mechanism that may retain the cap 34 on the refill 20. In other embodiments, other securement mechanisms may be utilized to retain the cap 34 on the refill 20. The first and/or second threads 72, 104 may include a single, contiguous thread, may be a double thread, or may be some other type of multi start thread. The first and/or second threads 72, 104 may alternatively be discontinuous.

Referring again to FIG. 3, an annular rim 110 is disposed at an upper end 112 of the neck 32 above the first thread 72. The rim 110 is defined by an interior surface 114, a top surface 116, and an outer surface 118, which will be discussed in greater detail hereinafter below. A first annular protrusion 120 extends outwardly from the neck 32 between the outer surface 118 of the rim 110 and the first thread 72. In some embodiments, the first annular protrusion 120 is included to retain the plug assembly 50, which may include a locking feature 122, as shown in FIGS. 3 and 4. The locking feature 122 may include a second annular protrusion 124 that snaps over the first annular protrusion 120. The neck 32 of the bottle 20 also includes an inner surface 130 that forms the channel 88. While the first and second annular protrusions 122, 124 are described as being annular, the first and second annular protrusions 122, 124 may alternatively be discrete, discontinuous protrusions.

Still referring to FIG. 3, the base 54 of the plug assembly 50 is shown in greater detail. The base 54 includes a well 140 defined by an inner wall 142, a lower wall 144, and an intermediate wall 146. The inner wall 142 and the intermediate wall 146 are substantially parallel. The lower wall 144 joins the inner wall 142 with the intermediate wall 146 and is further substantially perpendicular to each of the inner wall 142 and the intermediate wall 146. An upper wall 148 is joined with, and extends outwardly from the intermediate wall 146. The upper wall 148 is also coupled to an outer wall 152, which is substantially perpendicular to the upper wall 148. The second annular protrusion 124 is disposed along an inner surface 154 of the outer wall 152. In some embodiments, the inner wall 142, the intermediate wall 146, and the outer wall 152 are substantially parallel with respect to one another. In some embodiments, joints 156 between the inner wall 142 and the bottom wall 80, the lower wall 144 and the intermediate wall 146, the intermediate wall 146 and the upper wall 148, and the upper wall 148 and the outer wall 152 are rounded. Any wall or portion defined that is herein and is referred to as being substantially parallel with respect to another wall or portion may be up to 10 degrees offset from an axis defined by the first wall or portion.

Referring again to FIGS. 3 and 4, the cap 34 includes a seal skirt 160 that extends into the well 140 of the plug assembly 50. The seal skirt 160 may be dimensioned to abut the lower wall 144 of the plug assembly 50, thereby forming a seal therebetween. The seal skirt 160 may also be sized and positioned to provide a pressure or stress against a lower portion 150 of the intermediate wall 146, which can thereby relieve stress along the rim 110 of the neck 32 of the bottle 30. The seal skirt 160 may additionally or alternatively be sized and positioned to provide a pressure or stress against a medial portion 151 of the intermediate wall 146, i.e., a portion above the lower portion 150. The seal skirt 160 may have one or more features attached thereto or extending therefrom that can aid in relieving or displacing stress from the upper portion of the neck 32 of the bottle 30.

As shown in FIG. 4, the plug assembly 50 is secured to the bottle 30, and the cap 34 is secured to the plug assembly 50. The seal skirt 160 is disposed within the well 140 and abuts the medial portion 151 of the intermediate wall 146. Due to the geometry of the cap 34, the seal skirt 160 applies a pressure against the intermediate wall 146. A first seal is formed between the seal skirt 160 and the medial portion 151 of the intermediate wall 146, which is referred to as the "sheath-to-cap" seal. A second seal is formed between the intermediate wall 146 and the inner wall 130 of the neck 32, which is referred to as the "sheath-to-neck" seal. The sheath-to-cap seal and the sheath-to-neck seal prevent volatile from escaping from the refill 20 when the cap 34 is secured to the bottle 30, and when the plug assembly 50 is secured to the bottle, respectively. As such, each of the sheath-to-cap seal and the sheath-to-neck seal may be an air tight seal.

Figure 8:
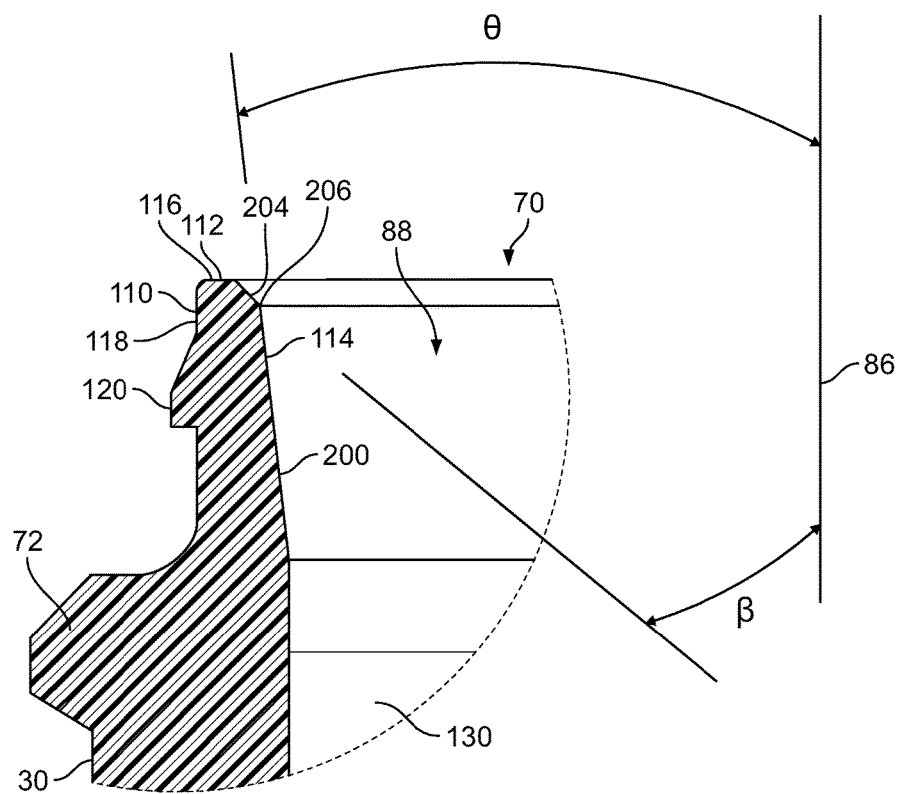
FIG. 8 is a partial cross-sectional view of a finish of the bottle of FIG. 7.

Referring to FIGS. 7 and 8, the configuration of the rim 110 of the bottle 30 will now be discussed in greater detail. Referring specifically to FIG. 8, to reduce the strain on the neck 32 of the bottle 30 and, thus, the stress cracks that can result therefrom, the interior surface 114 of the rim 110 is shown being angled, i.e., the interior surface 114 is a chamfered surface 200. In the embodiment illustrated in FIGS. 7 and 8, the chamfered surface 200 has a chamfer angle θ of approximately 6 degrees measured from the longitudinal axis 86. However, the chamfered surface 200 may have a chamfer angle θ of between about 1 degree and about 10 degrees, or between about 2 degrees and about 9 degrees, or between about 3 degrees and about 8 degrees, or between about 4 degrees and about 7 degrees, or about 6 degrees. In some embodiments, only a single portion or multiple discrete portions of the inner surface 130 of the rim 110 form the chamfered surface 200. In some embodiments, the entire inner surface 130 forms the chamfered surface 200. In some embodiments, the chamfered surface 200 begins at or above an uppermost extent of the first thread 72, as shown in FIG. 8, but the chamfered surface 200 may alternatively begin below an uppermost extent of the first thread 72.

Still referring to FIG. 8, the inner surface 130 of the rim 110 is partially defined by the chamfered surface 200 as well as an angled surface 204 that joins the chamfered surface 200 at an apex 206. The angled surface 204 may have an angle θ of approximately 45 degrees from the longitudinal axis 86. In some embodiments, the angle θ of the angled surface 204 is between about 20 degrees and about 70 degrees, or between about 30 degrees and about 60 degrees, or between about 40 degrees and about 50 degrees. The angled surface 204 terminates at the top surface 116 of the rim 110. The top surface 116 is generally perpendicular with respect to the longitudinal axis 86.

The benefits of the chamfered surface 200 will now be discussed. Through testing of existing refills, a high amount of stress was measured in the neck of the bottle. Further, it was determined that during assembly of existing refills, the high points of the stresses are generated at high interference locations, which were determined to be at each of the sheath-to-cap seal and the sheath-to-neck seal, as described above.

Through experimental testing, it was determined that a chamfered surface 200 of between about 4 degrees and about 7 degrees greatly reduces hoop stress in the neck 32 of the bottle 30 after the sheath 52 is inserted and retained within the neck 32, thereby reducing or preventing stress-cracking within the bottle neck 32 during assembly and/or when exposed to fragrance oils. The compression seal reduction from a first design of the bottle having a two degree chamfer for the sheath-to-neck seal resulted in an 8% stress reduction, and the sheath-to-cap seal resulted in a 6.7% stress reduction. For a five degree chamfered design, the sheath-to-neck seal resulted in a 9% stress reduction, and the sheath-to-cap seal resulted in a 20% stress reduction. It was determined that inclusion of the chamfered surface 200 moves the high interference locations down into the bottle neck by moving the high interference locations away from the bottle neck tip, where cracking typically occurs/originates.

During another test, the seal pressures and tensile hoop stresses developed during assembly of a refill with a six degree chamfer ("chamfered refill") were compared to the tensile hoop stresses developed for an existing mPP-based refill ("existing refill") with no chamfer. During the test, the chamfered refill and the existing refill were each filled with the same fragrance at room temperature, and were each assembled using a torque wrench. Both the chamfered refill and the existing refill were inverted quickly to allow for wetting of the bottle-sheath and sheath-cap contact surfaces. The mPP-based refill was otherwise identical in all relevant aspects (i.e., in the neck of the bottle) to the refill with the six degree chamfer. The seals of the chamfered refill were found to be at or better than the seals of the existing refill. For the existing refill, the peak sheath-to-neck seal pressure was found to be 1419 psi and the sheath-to-cap seal pressure was between 427 and 540 psi. For the chamfered refill, the sheath-to-neck seal pressure was found to be 1434 psi, while the sheath-to-cap seal pressure was between 520 and 726 psi. Both the chamfered refill and the existing refill were found to generate similar sheath-to-bottle compression seal pressures, while the chamfered refill maintained typical tensile hoop stresses in the neck. Maintaining the compression seals is important to ensure the fragrance remains within the bottle during transport and use thereof.

Any of the embodiments described herein may be modified to include any of the structures or methodologies disclosed in connection with different embodiments. Further, the present disclosure is not limited to substrate and/or support component shapes/sizes of the type specifically shown. Still further, the support components of any of the embodiments disclosed herein may be modified to work with various types of substrates consistent with the disclosure herein.

INDUSTRIAL APPLICABILITY

Numerous modifications to the present disclosure will be apparent to those skilled in the art in view of the foregoing description. Accordingly, this description is to be construed as illustrative only and is presented for the purpose of enabling those skilled in the art to make and use the device disclosed herein and to teach the best mode of carrying out same. The exclusive rights to all modifications which come within the scope of the appended claims are reserved.

We claim:
1. A refill for dispensing a volatile material, comprising:
 a bottle comprising:
  a body defined by at least one sidewall; and
  a neck extending outwardly from the at least one sidewall, the neck comprising a rim at an upper end of the neck, wherein the rim is defined by an inner surface, a chamfered surface, a top surface, and an outer surface,
a wick having a first end positioned within the bottle and a second end extending out of the bottle, the wick further defining a longitudinal axis;
a plug coupled to the neck of the bottle, the plug retaining the wick within the bottle; and
wherein the chamfered surface adjoins the inner surface of the rim, and
wherein the entire chamfered surface is tapered at an angle of between about 2 and about 9 degrees with respect to the longitudinal axis.

2. The refill of claim 1 further including a cap threadably engaged with the neck.

3. The refill of claim 1, wherein the rim further includes an angled surface that joins the top surface and the chamfered surface of the rim,
wherein the angled surface is disposed at an angle of between about 30 degrees and about 70 degrees with respect to the longitudinal axis.

4. The refill of claim 1, wherein the plug is defined by an inner wall forming a portion of a sheath around the wick, a lower wall joining the inner wall with an intermediate wall, and an upper wall joining the intermediate wall with an outer wall.

5. The refill of claim 4, wherein the inner wall, the lower wall, and the intermediate wall of the plug form a well, and
wherein a skirt of a cap is received within the well when the cap is secured to the refill.

6. The refill of claim 1, wherein the chamfered surface of the rim is tapered at an angle of between 4.5 and 6.5 degrees.

7. The refill of claim 1 further comprising a cap threadably attached to the neck of the bottle,
wherein an annular skirt of the cap extends into a well formed by one or more walls of the plug, and
wherein the annular skirt applies a force to a portion of the plug to reduce hoop stress in the neck of the bottle.

8. The refill of claim 7, wherein the skirt is in contact with a lower wall of the plug after the cap is secured to the bottle.

9. The refill of claim 1, wherein a volatile material including at least one fragrance oil is disposed within the body of the bottle.

10. The refill of claim 1, wherein a first annular protrusion is disposed along the outer surface of the rim between threading along the neck and the top surface of the rim, the first annular protrusion configured to interact with a second annular protrusion on the plug to secure the plug on the neck of the refill.

11. A refill for dispensing a volatile material, comprising:
a bottle comprising:
a body defined by at least one sidewall;
a neck extending outwardly from the at least one sidewall, the neck comprising:
threading circumscribing at least a portion of the neck; and
a rim at an upper end of the neck, the rim defined by an inner surface, a chamfered surface, an outer surface, and a top surface extending between the inner and outer surfaces;
a channel formed by the neck, a longitudinal axis being defined by the channel;
a wick having a first end positioned within the bottle and a second end extending out of the bottle, the wick being positioned within the channel;
a plug coupled to the neck of the bottle, the plug retaining the wick within the bottle and comprising a well formed by walls of the plug; and
a cap attached to the bottle, the cap comprising a seal skirt that extends into the well when the cap is secured to the bottle,
wherein the chamfered surface extends from the inner surface of the rim, and
wherein the entire chamfered surface is tapered outward from the longitudinal axis at an angle of between about 3 and about 8 degrees with respect to the longitudinal axis.

12. The refill of claim 11, wherein the plug comprises first and second spaced apart walls positioned within the channel and a lower wall connecting ends of the first and second spaced apart walls, with the well being formed by the first, second, and lower walls, wherein the seal skirt is in contact with at least one of the first and second spaced apart walls of the plug after the cap is secured to the bottle.

13. The refill of claim 11, wherein an inner surface of a securement portion of the cap includes a second thread that is capable of threadable engagement with the threading circumscribing the neck of the bottle.

14. The refill of claim 11, wherein a volatile material including at least one fragrance oil is disposed within the body of the bottle.

15. The refill of claim 11, wherein a first annular protrusion is disposed along the outer surface of the rim between the threading and the top surface of the rim.

16. The refill of claim 15, wherein a second annular protrusion is disposed along an inner surface of an outer wall of the plug,
wherein the second annular protrusion snaps over the first annular protrusion to retain the plug on the neck of the refill.

17. The refill of claim 11, wherein the chamfered surface of the rim is tapered at an angle of 6 degrees.

18. The refill of claim 11, wherein the bottle is made of a polymer.

19. The refill of claim 11, wherein the plug further includes a sheath extending from a base of the plug, wherein the sheath covers more than half of an upper portion of the wick.

20. The refill of claim 19, wherein the chamfered surface of the rim is tapered around the entire rim.

21. The refill of claim 11, wherein the rim further includes an angled surface that joins the top surface and the chamfered surface of the rim,
wherein the angled surface is disposed at an angle of between about 30 degrees and about 70 degrees with respect to the longitudinal axis.

* * * * *